(12) United States Patent
de Andrade

(10) Patent No.: US 7,588,546 B2
(45) Date of Patent: Sep. 15, 2009

(54) BIOPSY GUN AND SURGICAL INSTRUMENT

(76) Inventor: Eugenio Machado de Andrade, Rua Canário, 515 - Ap. 51, São Paulo, SP 04521-002 (BR)

( * ) Notice: Subject to any disclaimer, the term of this patent is extended or adjusted under 35 U.S.C. 154(b) by 0 days.

(21) Appl. No.: 11/646,748

(22) Filed: Dec. 28, 2006

(65) Prior Publication Data

US 2007/0179402 A1    Aug. 2, 2007

(30) Foreign Application Priority Data

Jan. 3, 2006    (BR) ................................ 8600004 U

(51) Int. Cl.
*A61B 10/00*    (2006.01)
(52) U.S. Cl. ........................ 600/567; 600/564; 600/568
(58) Field of Classification Search .................. 600/564, 600/562, 567, 568
See application file for complete search history.

(56) References Cited

U.S. PATENT DOCUMENTS 5,546,957 A *    8/1996    Heske ........................ 600/564
2004/0153002 A1*    8/2004    Schramm ..................... 600/564

* cited by examiner

*Primary Examiner*—Max Hindenburg
*Assistant Examiner*—Emily M Lloyd
(74) *Attorney, Agent, or Firm*—D. Peter Hochberg; Sean F. Mellino; Daniel J. Smola

(57) ABSTRACT

A biopsy gun and surgical instrument for practical and innovative sample collecting of biopsies in the field of medical diagnosis. The biopsy gun and surgical instrument contains an interchangeable connector system which allows for the usage of needles of the most diversified models, sizes and diameters existing in the market. The biopsy gun and surgical instrument enables usage of such various needles without the need to change the whole grip of the biopsy gun.

10 Claims, 16 Drawing Sheets

BIOPSY GUN AND SURGICAL INSTRUMENT

RELATED APPLICATION

This application claims foreign priority based on Brazilian Application Serial No. MU8600004-7, filed on Jan. 3, 2006, the content of which is incorporated herein by reference in its entirety.

BACKGROUND OF THE INVENTION

1. Field of the Invention

The present invention relates to a practical and innovating sample collector for biopsies in the medical field. More specifically, the present invention relates to a sample collector for diagnostic medicine for improving its usage and performance in relation to other models usually found in the market.

2. Description of the Prior Art

The diagnostic medicines are an area of medical sciences which has vital importance in a large number of different pathologies. One of the most important of which for physicians and patients are the neoplasies, known as cancer.

The characteristic of cancer is the disarranged multiplication of cells, which lose their growth control and no longer respect the tissue structures.

Later, when cells get into the blood circulation, through vessels and arteries and mainly into the lymphatic circulation, cancer is spread out to other organs. This phase of the disease is known as metastasis, and leads to the organs' failure which may cause death.

The diagnosis of this kind of pathology has always been a challenge to medicine. The appearance of computerized tomography and image exams made the advancement in treatment of cancer remarkable. However, there is a diagnosis resource even more indispensable than those exams: the biopsies.

Biopsy is a clinical exam procedure which consists of the removal and pathological evaluation of tissue samples, as small fragments of a live body. They are extremely important to enable the physician to establish a diagnosis and observe the treatment evolution. They are used not only for diagnosis of neoplasies, but also in monitoring cases of transplanted organs, suspicion of insufficiency of operation of organs and tissues, and for following up medicinal treatments, among others.

Currently, there are two kinds of biopsies: cytological biopsies and histological biopsies. The cytological biopsy is an aspirating puncture carried out through the use of a thin-sized needle. It is a positive procedure usually guided by ultra-sonography, for aspiring cysts or the content of nodes or tumors. The histological biopsy consists of a percutaneous procedure in which, through a system of coaxial needles, a small sample of tissue is collected where the injury is located. The advantage of histological biopsy over the cytological one is that, by obtaining a sample of removed material instead of a sample of aspirated material, groups of complete cells are obtained instead of insulated cells. In addition to that, the collected material is highly concentrated and not diluted by fluids of tissues and blood, as in an aspirated biopsy. This material eases the microscopic examination, rendering the histological biopsy more reliable.

The histological biopsy uses a biopsy sample collector or grips which comprise a body, to protect the needles and aid its handling. The biopsy sample collector or grips serve as a guide to slide the stem and the collecting needle. The needles and the stems used in the procedure are disposable and intended for a single use, in order to assure the proof of efficiency, sterility and uncontestable safety against any kind of accidental inoculation. There are two main types of instrument grips: the disposable and non-disposable ones.

Among the disposable models are the needles with a semi-automatic guillotine-cutter, which are simpler instruments in construction since they include a grip in which the needle itself is already coupled. The model commonly used includes disposable grips, which follow the same principle of needles having a semi-automatic guillotine-cutter.

The non-disposable models are similar to the grips of disposable ones; however, they are produced from resistant and sterilizable material, which allows the grip to be repeatedly used after the sterilization by heating or by gas.

It is well known that accuracy and quickness are required from medical people, especially in the surgical area. In order to help to comply with these requirements, there is the advent of surgical materials, such as the grips for collection of biopsy samples previously mentioned. However the current equipment is deficient, which ends up hindering the surgeon's work even more when carrying out the biopsy.

The disposable models are practical and are more cost-effective than other equipment. However, they do not provide the surgeon with the accuracy necessary for the procedure. These are more often used in case of injury to tissues closer to tegumentar tissue.

The non-disposable grips are more reliable owing to the needle's coaxial sliding system. However, the equipment is more expensive, in spite of being reused after sterilization. There is a great number of different needles in the market, with different sizes and lengths, adapted to the organ from where the sample will be collected. There is also a diversity manufacturers of these needles and grips. The main problem with these models is the fact that the grips are not adaptable to the different types of needles, and the physician needs to have a compatible model for each type of needle, including size and length, in order to use them effectively.

In addition to this inconvenience, there is also a deficiency in the drive system of the control knob for the devices that currently exist in the market. Owing to the complexity of the system, it becomes difficult for the physician to properly perform the procedure. As those qualified in the surgical area are aware, the collection of biopsy samples is a procedure which requires much attention and accuracy from the surgeon, since the areas to be explored may be extremely small. The least deviation in the process and the diagnosis is compromised. In the current systems, the trigging drive and positioning system, which includes a spring system, is complicated and makes the procedure difficult and leads to a higher risk of failure when collecting the tissue.

SUMMARY OF THE INVENTION

It is, however, one object of the present invention to supply a sample collector for biopsies, with a device in which not only the operational quantities have been considered in the manufacturing design, but also the form, the disposition and the localization of its parts and components which, when correctly positioned will provide more safety to the process without any increase in cost.

It is another object to provide an efficient biopsy sample collector, which provides more reliability in its purpose, by both its operational characteristics as well as by its ease of use.

The foregoing objects are obtained by the provision of a discharging mechanism located on the front part of its body. This positioning allows the surgeon to activate the device with his indicating finger or thumb, providing an accurate placement of the needle to the tissue target place. Since it can be operated with one of the surgeon's hands, it helps the use in procedures requiring other instruments, such as viewing instruments, for example ultra-sound devices.

The triggering and positioning of the needle through the grip is delicate and high risk, since any little deviation may impair the procedure. With that in mind, a safety lock system has been developed which avoids accidental discharge and provides the surgeon with more comfort and reliability when triggering and positioning the needle at the position necessary for collection.

The needle sliding system enables the sample removal without the need for moving the instrument needle, which further reduces the risk of sample violation, which could contaminate it, thus compromising the result of the examination. The instrument dimensions have been optimized to lessen the trauma risks and maximize the stability during the procedure. This second factor is of paramount importance, in order to provide accuracy of the sample collection, since unnecessary insertion of the stem into several directions can be avoided.

The head fitting system does not require the use of screws or locks, since they are kept positioned through cylindrical fittings and powerful magnets. The lid is articulated and is provided with a magnetic locking system. This differential may be extremely important with respect to an instrument used in a surgical procedure, as in the case of biopsies. The use of pins, locks or screws require holes to be made on the part. These holes can be the entrance for bacteria and microorganisms, which may contaminate the sample, compromising the exam result, or even contaminate the patient himself/herself, causing irreversible damages to his/her health.

The head replacement system allows the use of several different models, sizes and diameters of needles existing in the market, without the need for replacing the whole part. The replacement of the interchangeable elements positioned on the upper faces of the movable bases: instead of a finger grip to each type of needle, there is a small part, able to be fitted into the grip for each type of needle. Since it is a grip whose parts can be changed so as to be adapted to each type of needle, a constant movement of pins, locks and screws could lead to excessive wear and tear to the equipment. This is an additional advantage of the fixing system by magnets to the consumer.

Another object of the present patent is to provide a biopsy sample collector that can be manufactured from sterilizable material, so that after each sample collection procedure, a sterilization process is carried out through conventional methods. This allows the grip to be re-used in another patient, efficiently and without risk of contamination, in addition to lessening costs of equipment. In case another type of needle with a different type of fitting from the ones existing in the market is developed, new heads can be used with a suitable fitting system suitable for each type, whereby an innovative and highly adaptable device to the market needs has been provided pursuant to the invention.

The present invention in its preferred form is a sample collector to be used with a selected one of at least two types of a stem and needle. Each type of a stem and needle has a different structure. The sample collector cooperates with the respective different structures to operatively receive the selected type of a stem and a needle. The sample collector has a grip serving as a housing, first and second movable bases, a plurality of interchangeable connectors having fitting elements for cooperating with the respective different structure of the different types of a stem and needle. The movable bases each having interchangeable connector positioning structure, which can be at least one projection extending from the movable base, and is preferably three cylindrical projections having progressively larger diameters extending from the upper face of the movable base. The interchangeable connectors each have a locating structure, which can comprise a receptacle in the interchangeable connector for the respective projections, which in the preferred embodiment are three holes with progressively larger diameters. The interchangeable connectors have fitting elements for cooperating with the different structure on the different types of a stem and needle, and the appropriate interchangeable connector with the fitting elements that cooperate with the respective different structure of the different types of a stem and needle is selected. Releasable holding apparatus is preferably provided for holding each interchangeable connector to one of the movable bases, and the releasable holding apparatus is preferably one or more magnets, and the part being attracted to the magnet is magnetic. A main monoblock is provided for affixing in an operative relationship the movable bases and the interchangeable connectors. Slotted cylindrical holes extend through the movable bases, and a cylindrical rod having transverse projections extends through the bases. The cylindrical axle can either be positioned so the projections are located in the slots to permit movement of the movable bases, or the axle can be rotated so that the projections engage a shoulder at the end of the partial cylindrical walls to lock the movable bases in place.

BRIEF DESCRIPTION OF THE INVENTION DRAWINGS

DETAILED DESCRIPTION OF THE PRESENT INVENTION

The object of the present patent comprises an improvement introduced to an instrument for biopsy sample collection, which comprises a grip (1) which serves as a base to the needle coupling (3) and a disposable stem (4) for collecting tissue samples.

Figure 1:
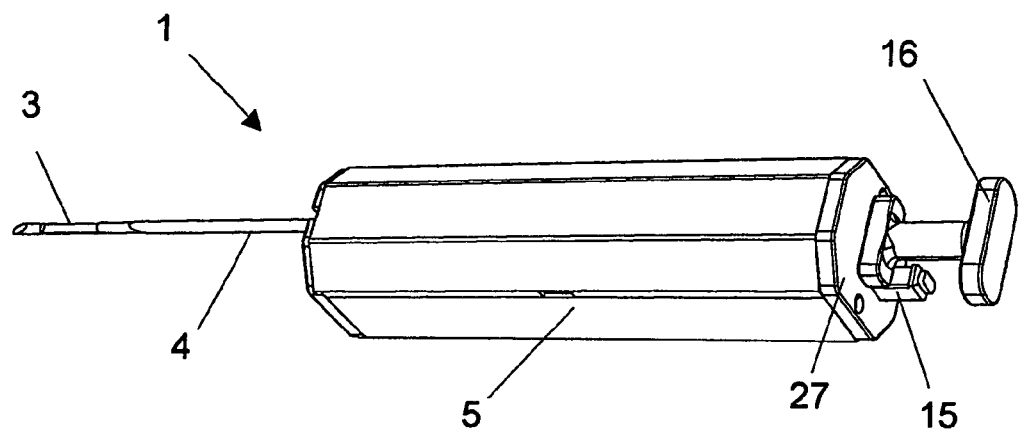
FIG. 1 is an upper-rear perspective view of the grip assembled with needle and stem, according to the present invention.
Figure 2:
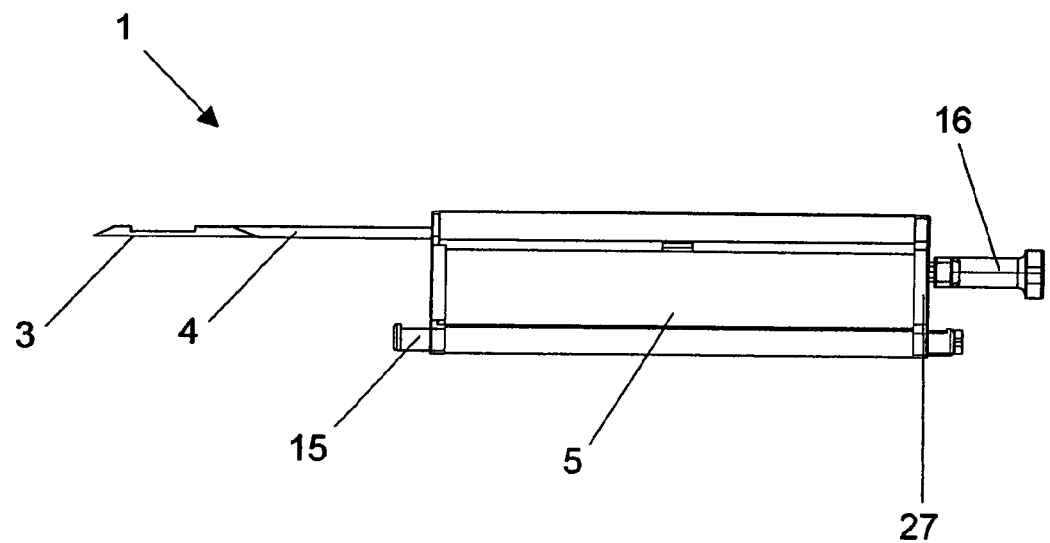
FIG. 2 is a side view of the grip assembled with needle and stem.
Figure 3:
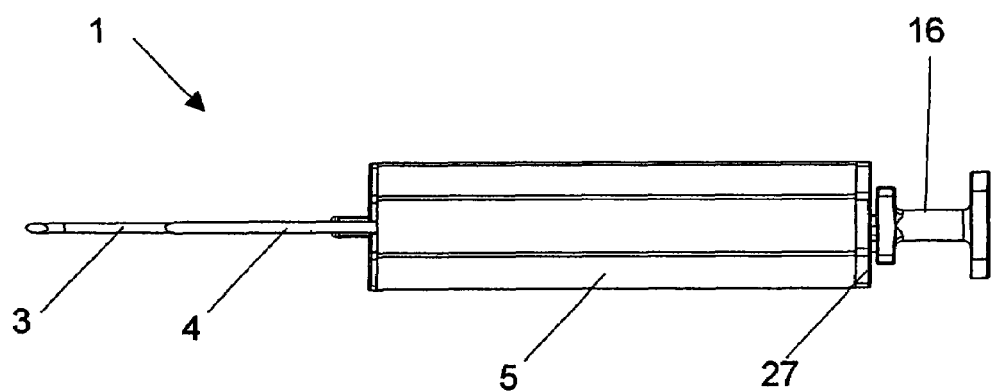
FIG. 3 is an upper view of the grip assembled with a needle and stem.
Figure 4:
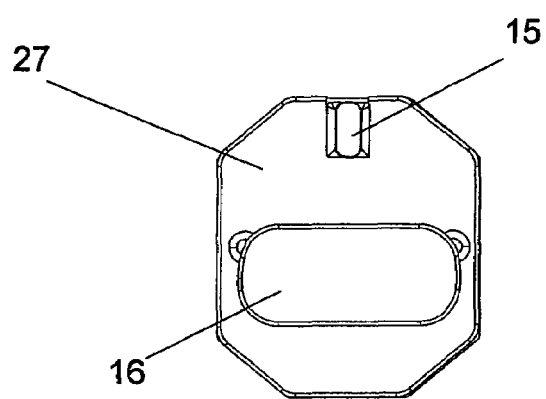
FIG. 4 is a rear view of the grip, pointing out the handle area.
Figure 5:
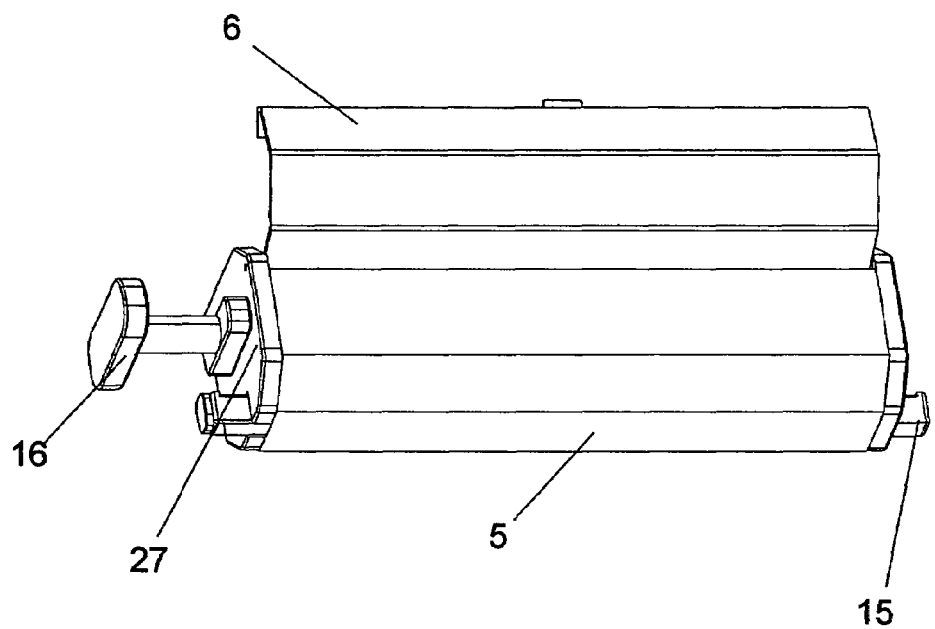
FIG. 5 is a side perspective view of the grip with the lid open, without the needle and stem.
Figure 6:
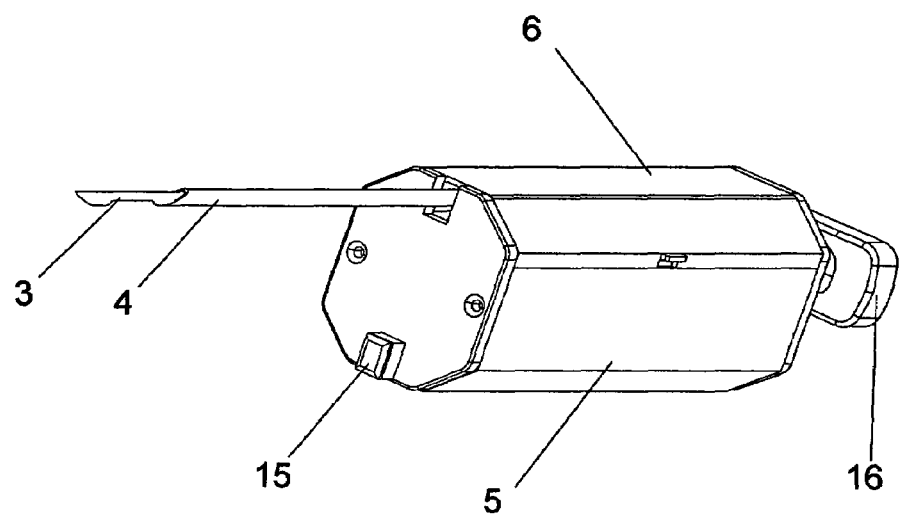
FIG. 6 is a frontal perspective view of the grip assembled with the needle and stem.
Figure 7:
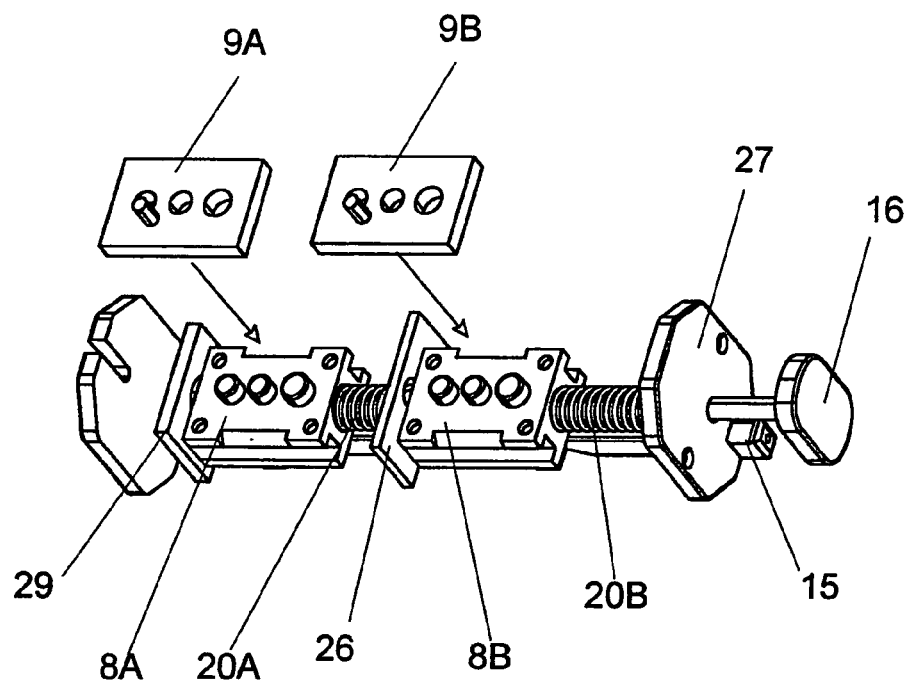
FIG. 7 is an upper front perspective view of the needle moving system and of the stem, showing the fitting of the interchangeable elements of the grip.
Figure 8:
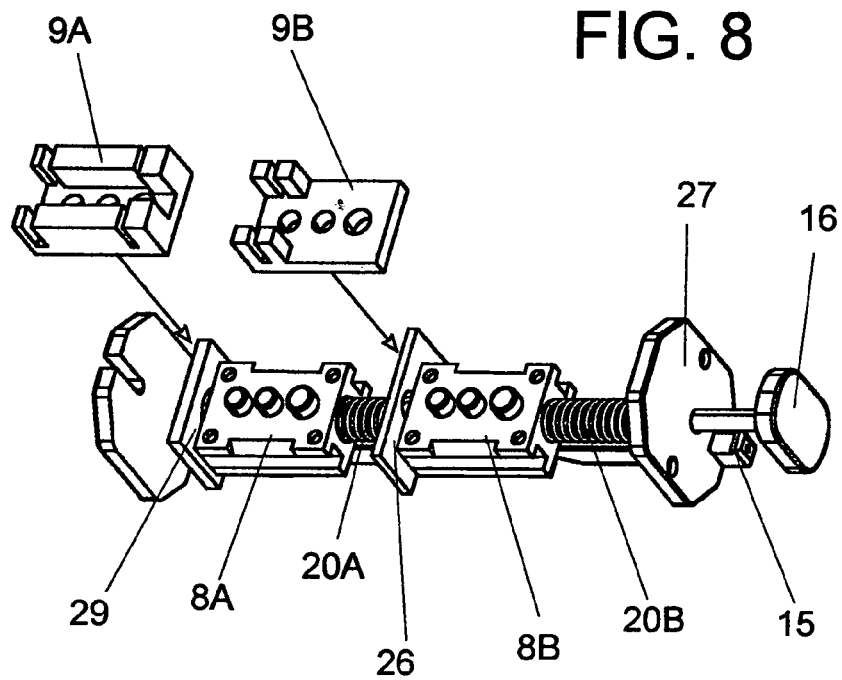
FIG. 8 is a frontal upper perspective view of the needle and stem moving system, showing the fitting of the interchangeable movements, with the needle and stem different from the ones presented in FIG. 7.
Figure 9:
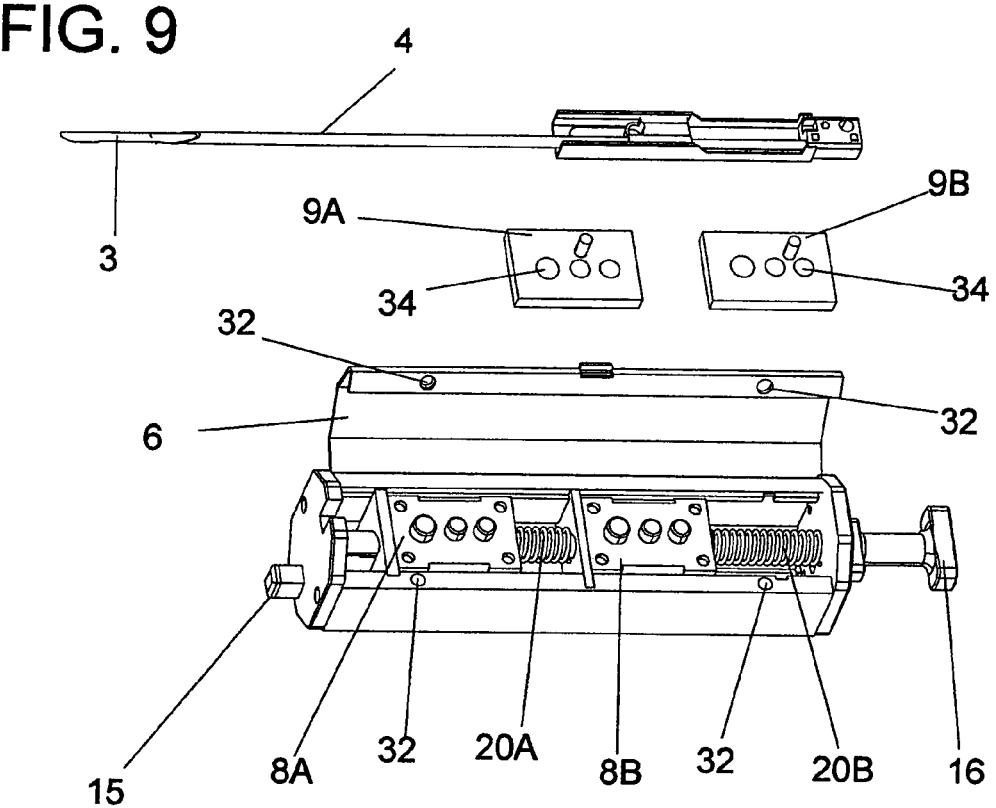
FIG. 9 is a side upper perspective view of the moving system of the needle and stem, showing the fitting of the interchangeable movements and of the needle and stem on the grip.
Figure 10:
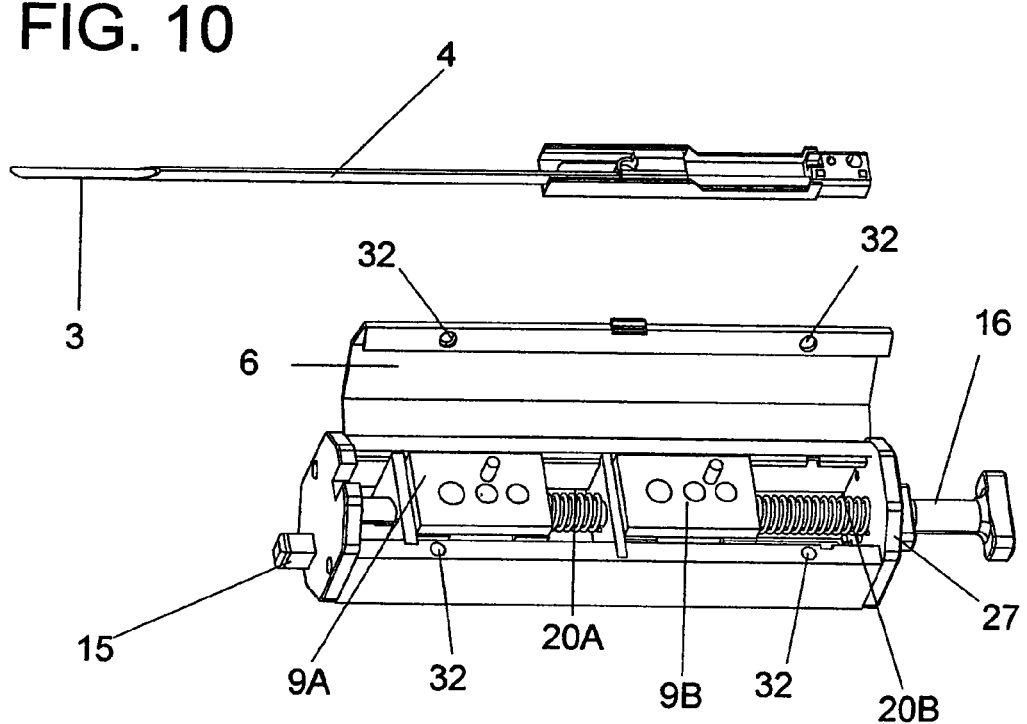
FIG. 10 is a side upper perspective view of the moving system of the needle and stem, showing the fitting of the needle and stem on the grip.

The grip (1) is produced from hard and sterilizable material and comprises a quadrangular structure (5), with an articulated lid (6) which has magnets (32) of sufficient strength on its ends for an efficient locking with quadrangular structure (5) as shown in FIGS. 9 and 10. A fixture or main monoblock 7 is provided in the inner portion, where the parts of the grip mechanism are fixed (1).

Figure 14:
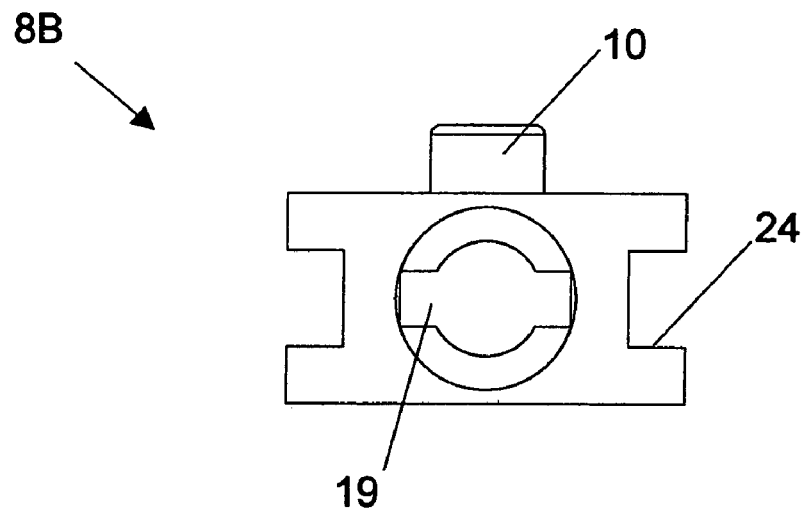
FIG. 14 is a frontal view of the base.
Figure 15:
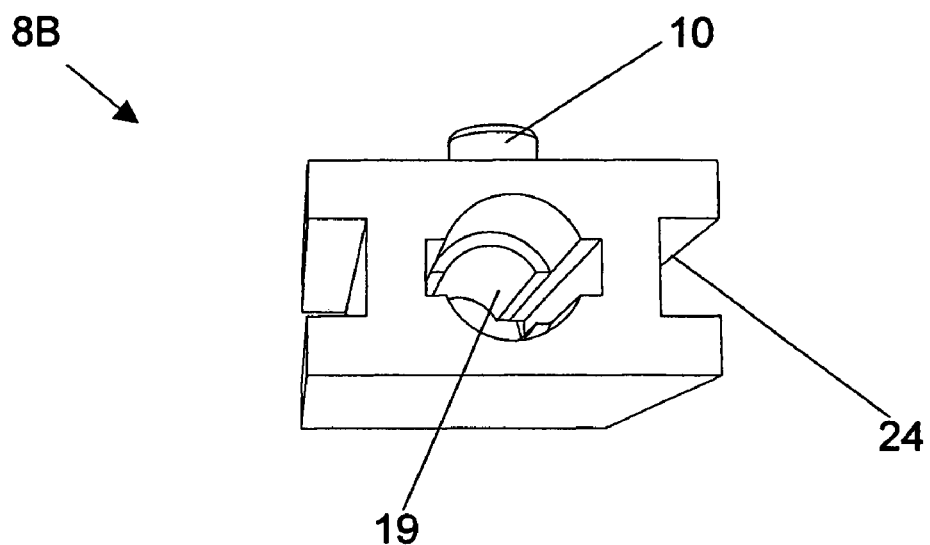
FIG. 15 is a frontal lower perspective view of the base.
Figure 16:
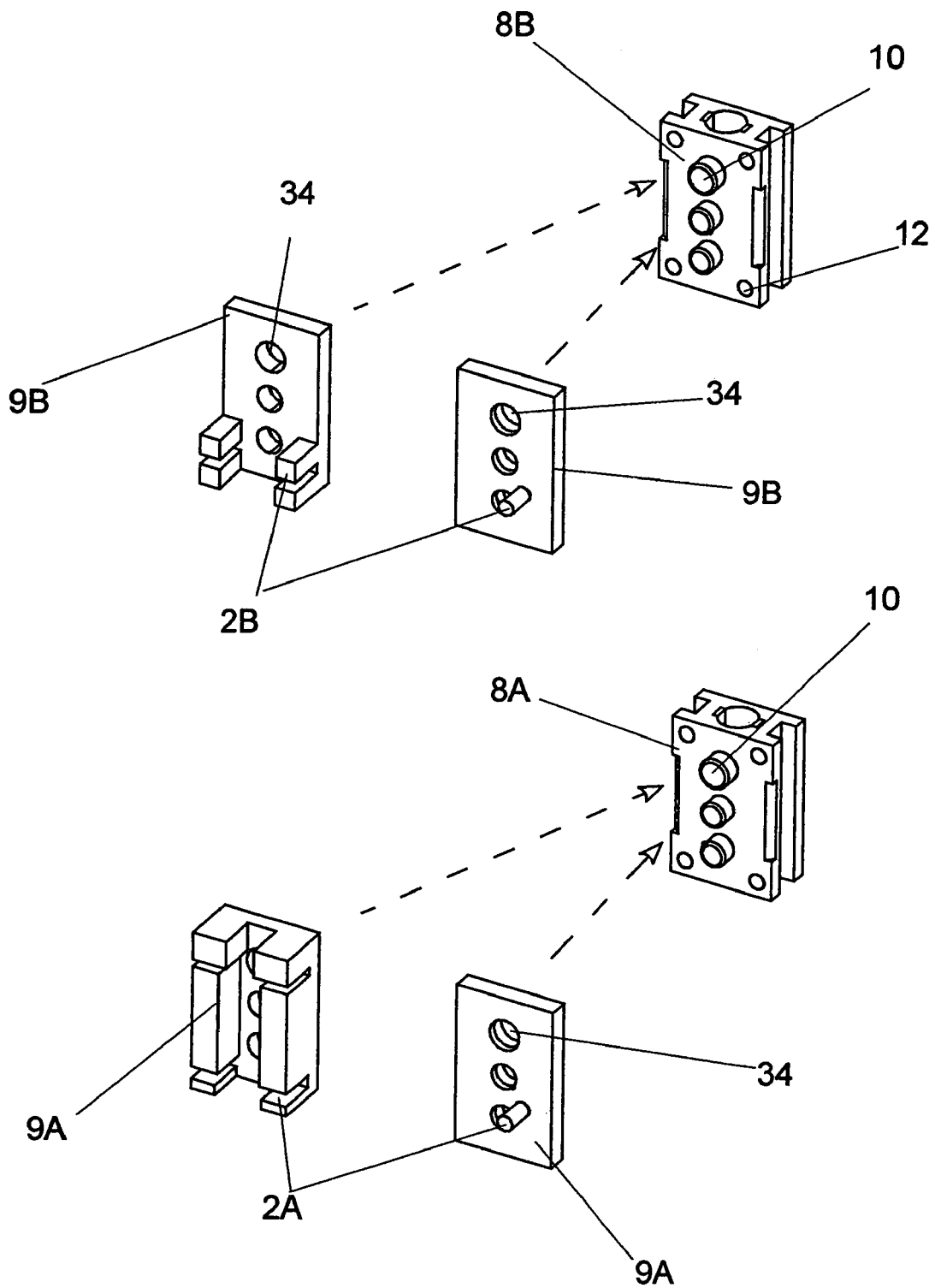
FIG. 16 is a frontal upper perspective view of the base of the interchangeable movements, showing the fitting.
Figure 17:
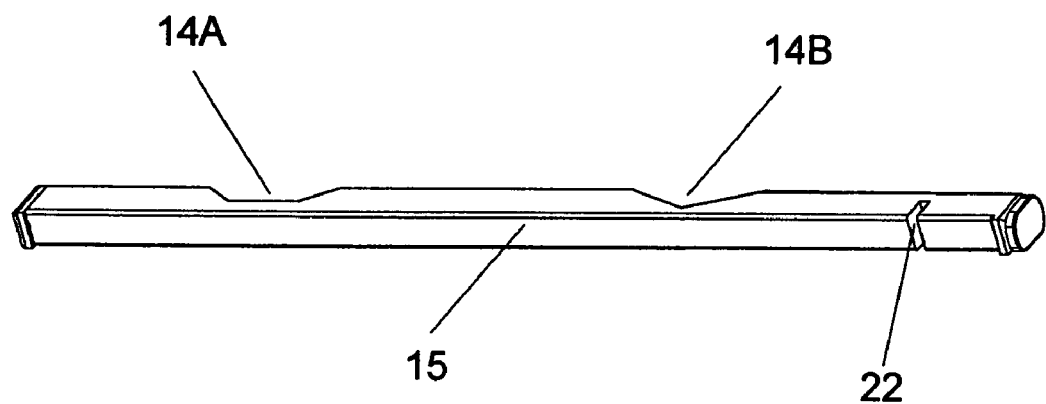
FIG. 17 is a side upper perspective view of the rectangular axle, pointing out the grooves where the safety lock is fitted and the retention sliding elements.
Figure 18:
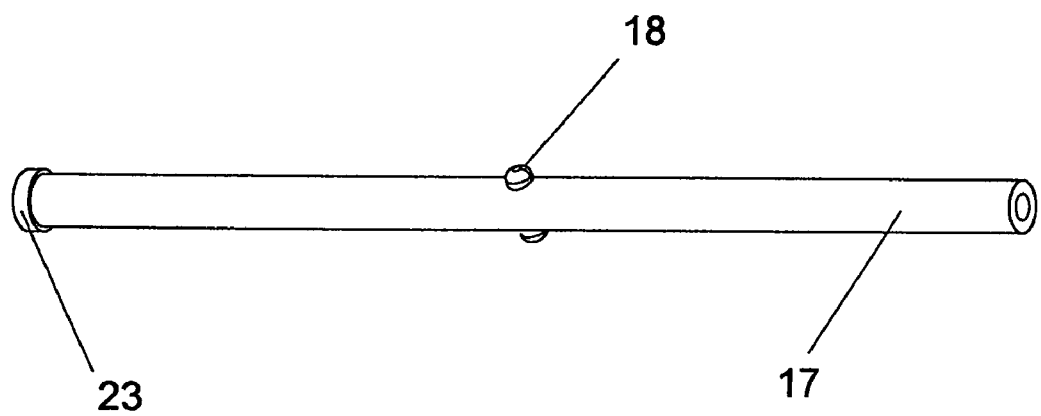
FIG. 18 is a side upper perspective view of the cylindrical axle, pointing out the projections on its central part and a slightly bigger diameter on one of its ends.
Figure 19:
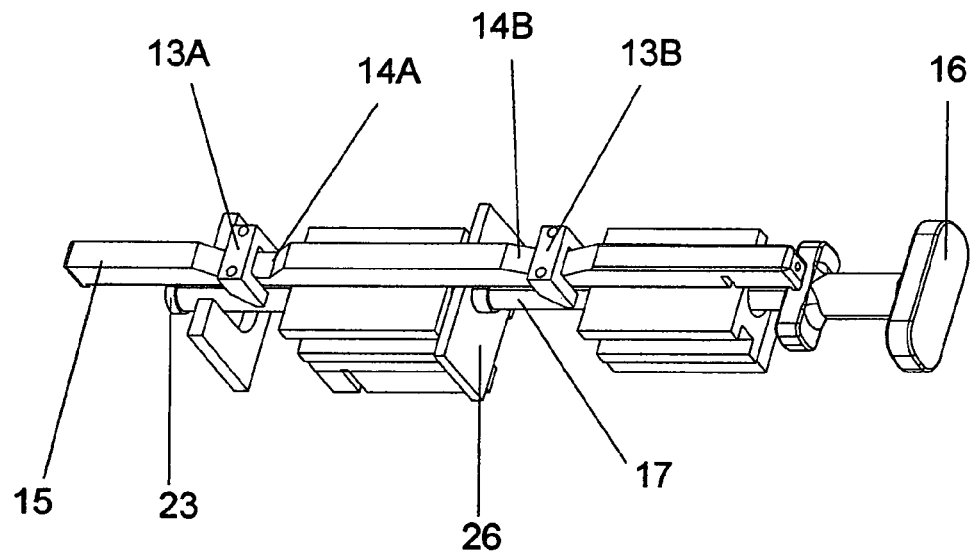
FIG. 19 is a side lower perspective view of the system of positioning and locking of the needle and stem.
Figure 20:
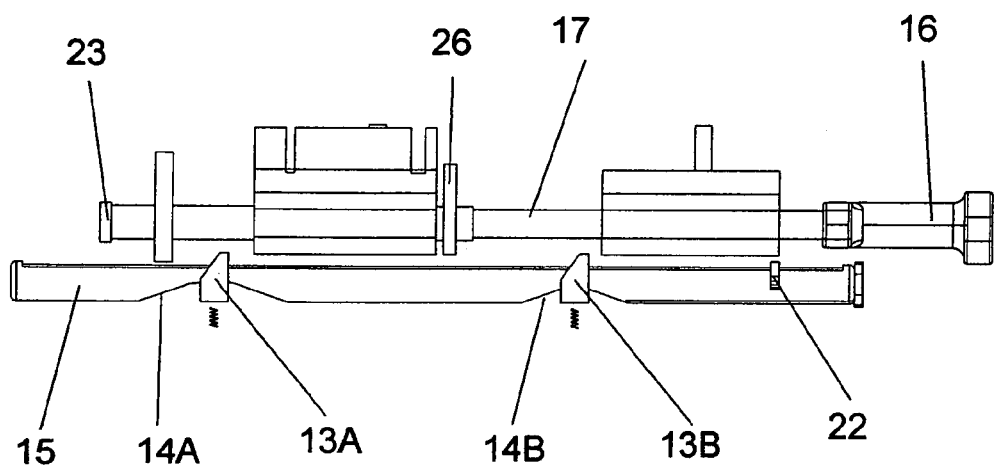
FIG. 20 is a side view of the positioning system and of the locking of the needle and stem.
Figure 21:
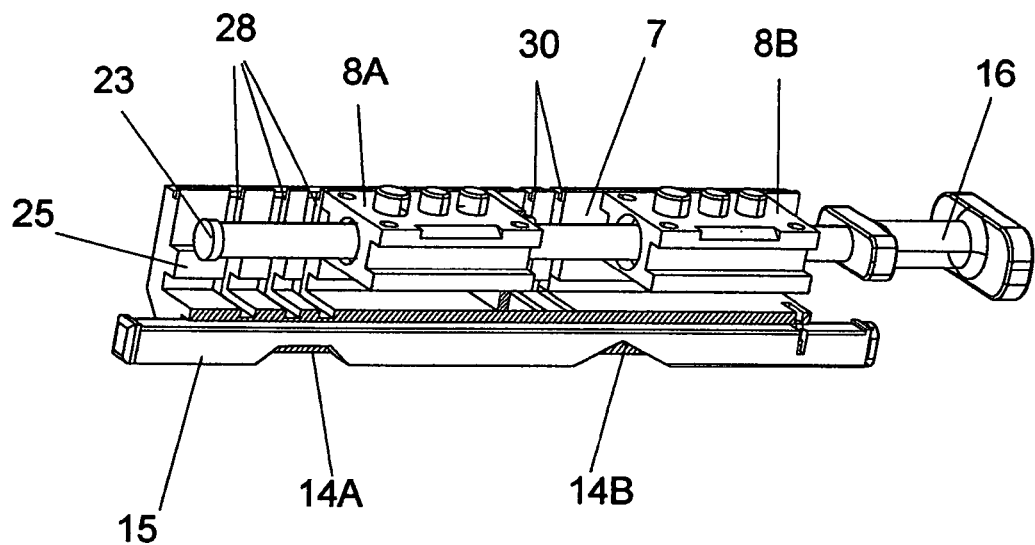
FIG. 21 is a side upper perspective view of the grip, with a longitudinal cut pointing out the positioning of the rectangular axle cut in relation to the bases.
Figure 22:
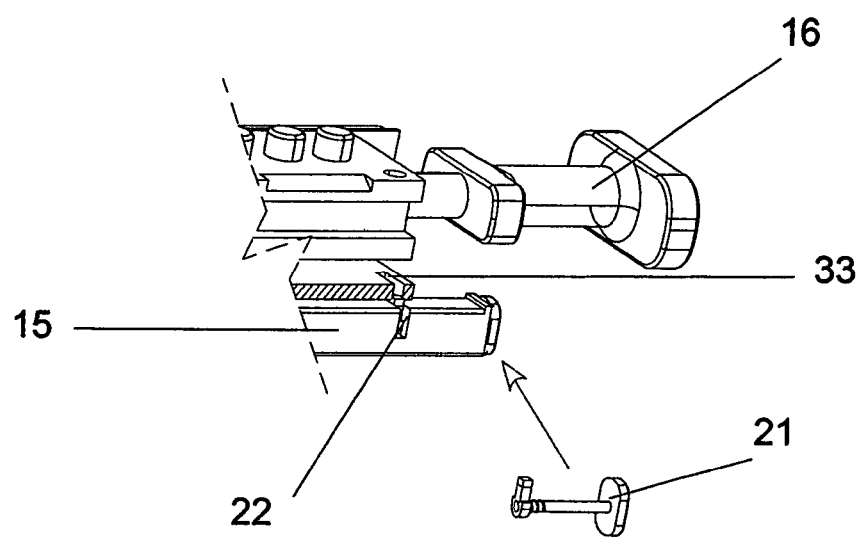
FIG. 22 is a side upper perspective view of the safety lock system detail of the grip.
Figure 23:
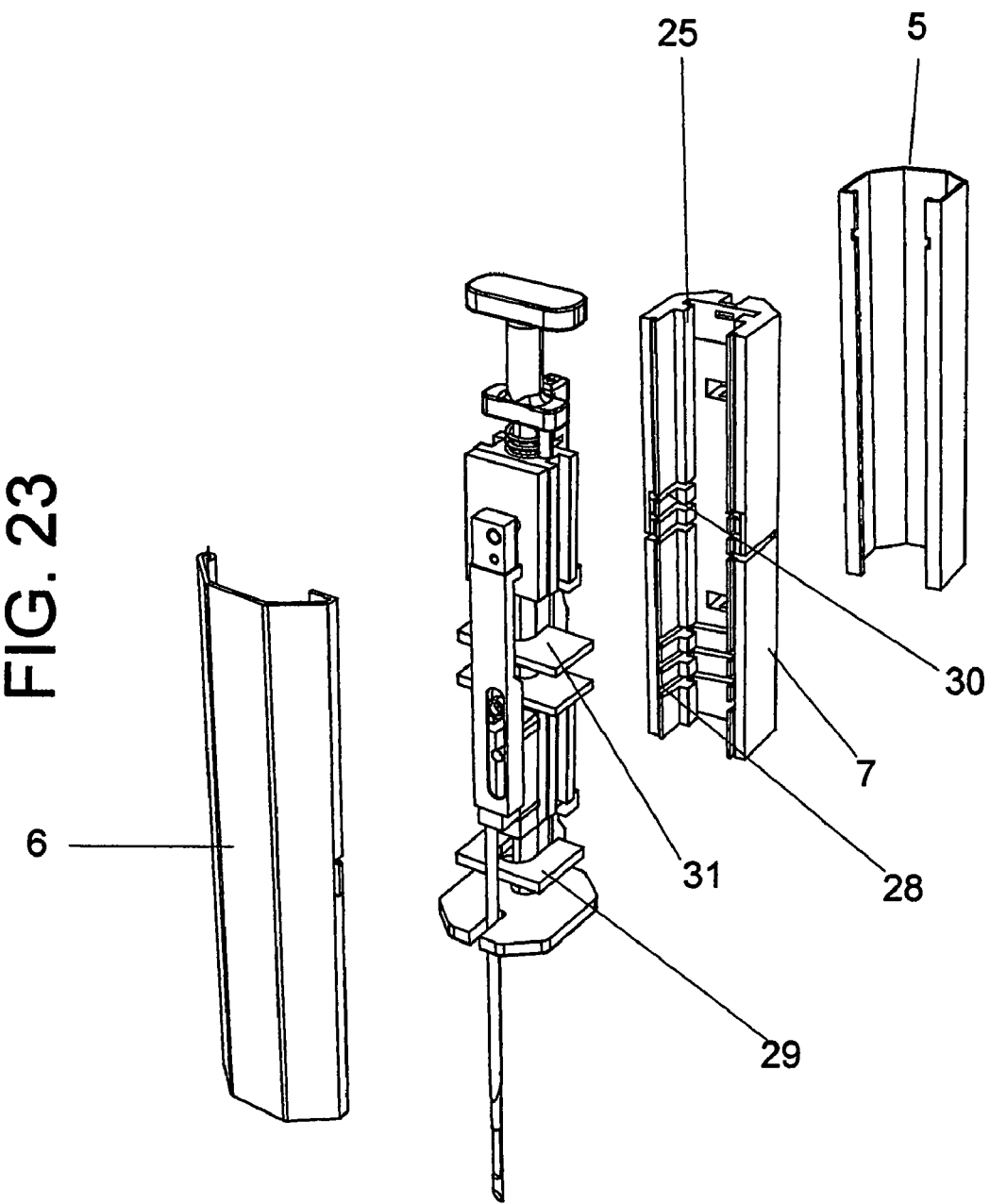
FIG. 23 is an exploded side upper perspective view of the grip.
Figure 24:
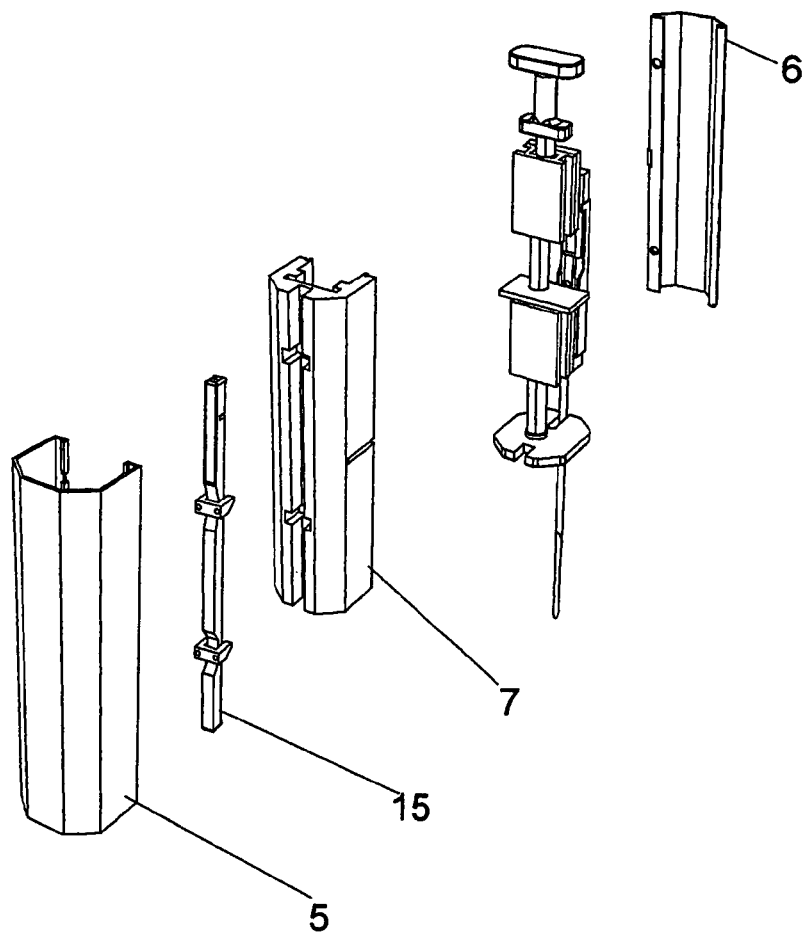
FIG. 24 is an exploded side lower perspective view of the grip.
Figure 25:
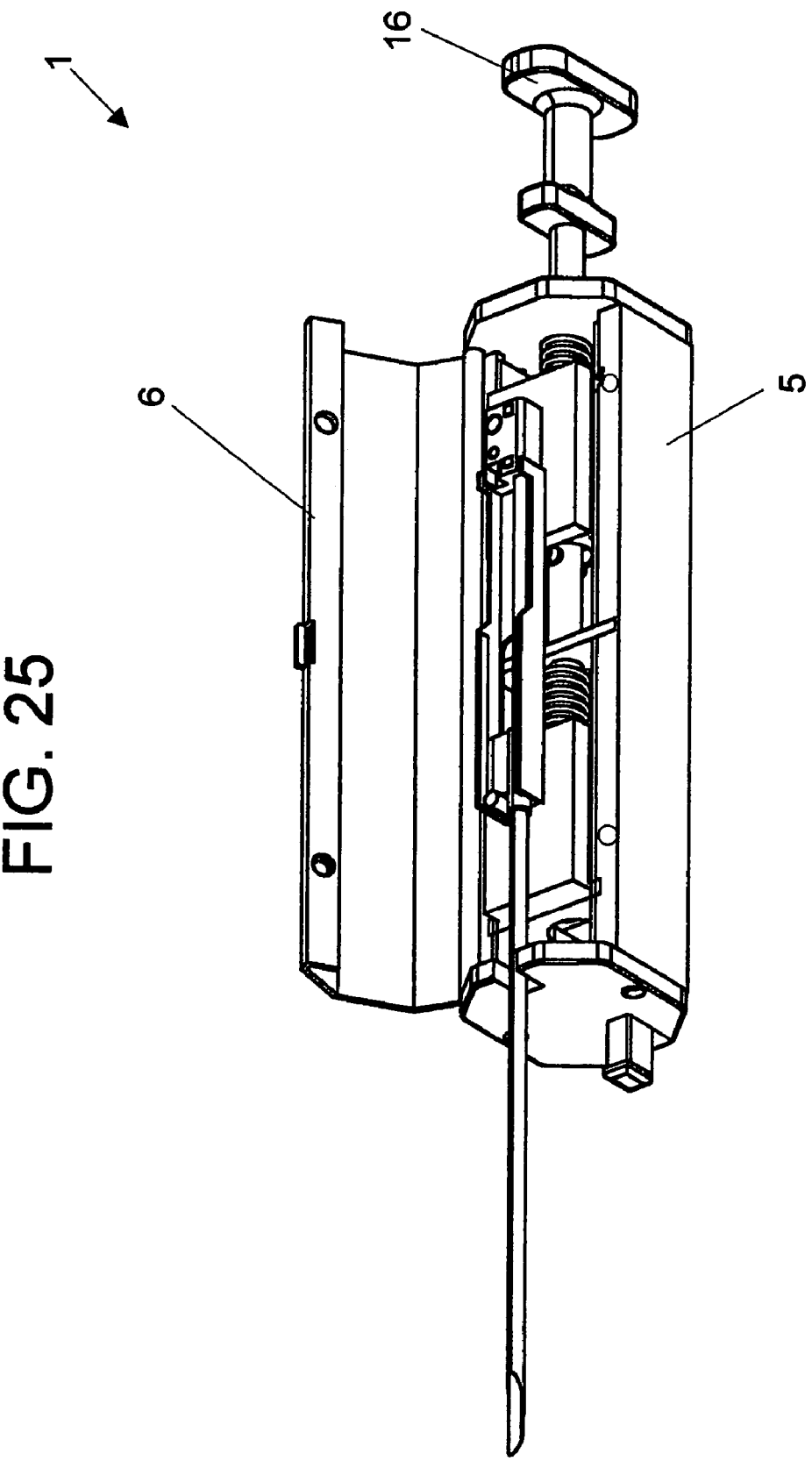
FIG. 25 is a frontal upper perspective view of the grip assembled with a certain type of needle and stem.
Figure 26:
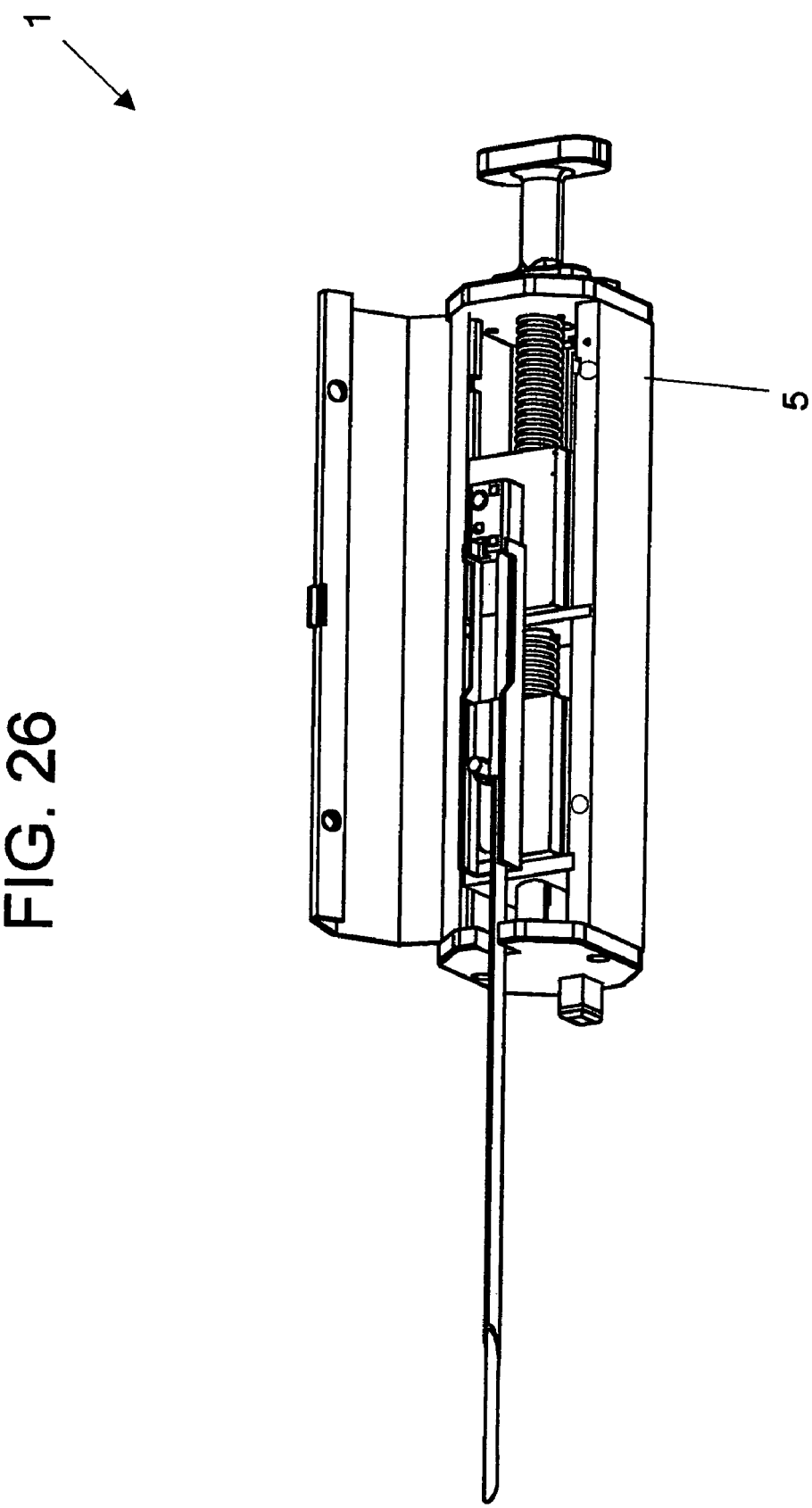
FIG. 26 is a frontal upper perspective view of the grip assembled with a type of needle and stem, different from the one presented in FIG. 25.

The present instrument has movement which takes place through a system composed of two movable bases (8A) and (8B) parallelepiped format with side guides formed by longitudinal cuts (24) of rectangular section on both sides and fitted into rectangular longitudinal projections (25) provided on the mono-block sides (7). Three cylindrical projections (10) are provided on the upper faces of the bases (8A) and (8B) and are positioned linearly and longitudinally to the sizes progressively bigger. This constructive disposition was established for reducing the high costs associated with the acquisition of equipment. As mentioned before, the current sample collectors of high instrumental quality require the surgeon to have a grip for each type of needle (3) existing in the market. As shown in FIGS. 14 and 15, base (8B) also comprises a hole (19) in the central and longitudinal axle of circular section with two rectangular openings opposed by the center.

Holes (12) are provided on the vortexes of the bases which have powerful magnets in their inner side (11). Fitted on their upper face are interchangeable elements called intermediate connectors (9A) and (9B), which have holes (34) matching the cylindrical projections (10). The upper face of the intermediate connectors (9A) and (9B) has fitting elements (2A) and (2B) standardized with the set of stems (4) and needles (3) existing in the market, that is, the surgeon only needs to acquire a single grip (1) and only two parts of intermediate connectors (9A) and (9B) for adapting to the use of a new mark or type of needle (3) necessary to carry out the procedure. That is, interchangeable elements (9A) and (9B) have a fitting position defined by the holes (34) foreseen on their body and by cylindrical projections (10) of the bases (8A) and (8B). Interchangeable elements (9A), (9B) are fixed by magnets (11) fitted on the bases (8A) and (8B).

Figure 11:
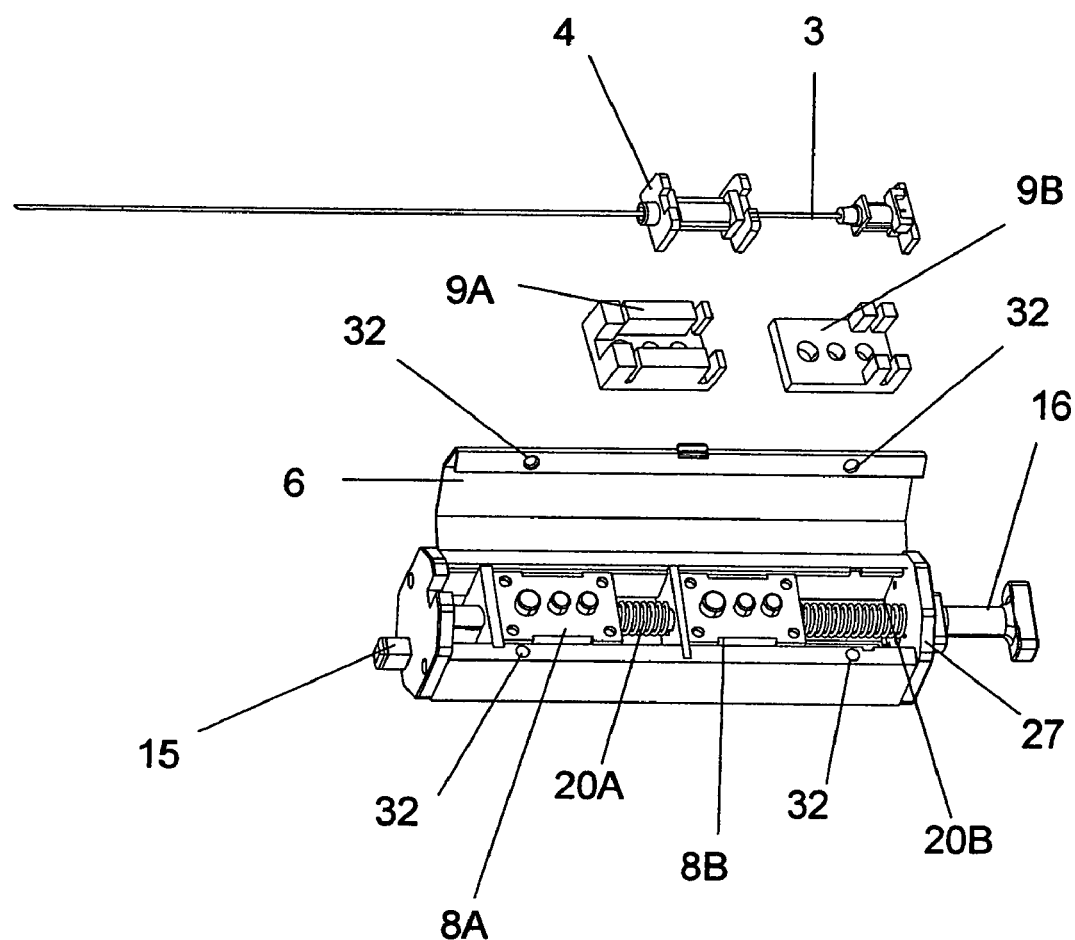
FIG. 11 is a side upper perspective view of the moving system of the needle and stem, showing the fitting of the interchangeable movements and of the needle and stem on the grip.
Figure 12:
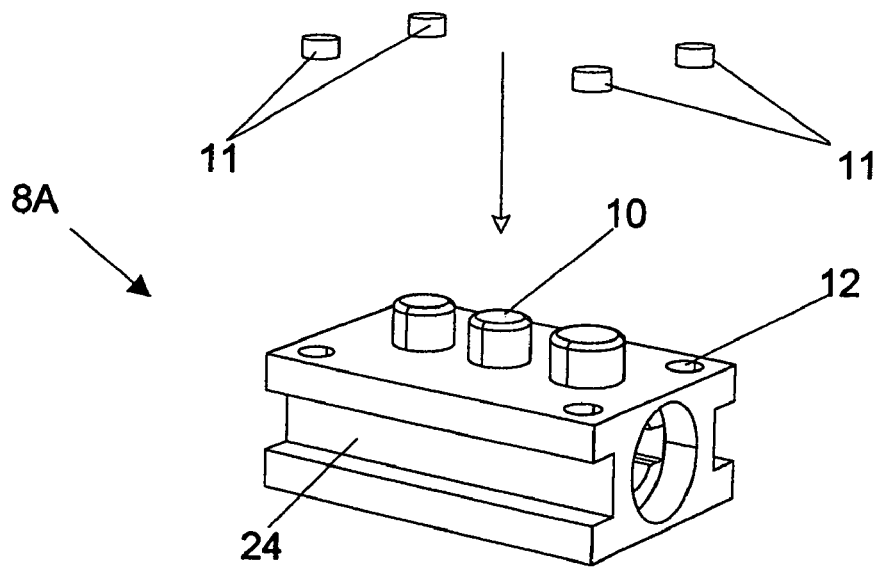
FIG. 12 is a side upper perspective view of the base, showing the position of magnet insertion.
Figure 13:
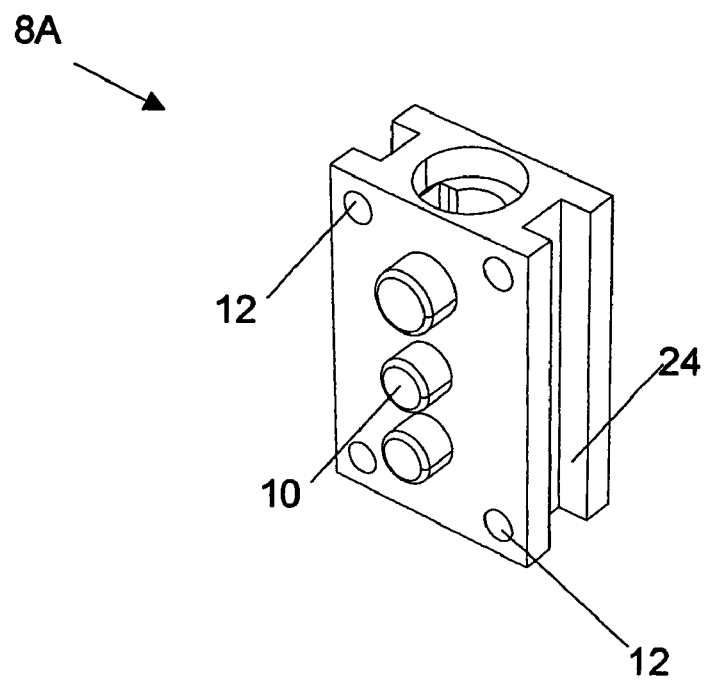
FIG. 13 is a front upper perspective view of the base.

The referred grip (1) was designed to enable the coupling of several types of needle and (3) stem sets (4) existing in the market, through the use of intermediate connectors (9A) and (9B) adapted to the set of stem and needle which is intended to be used. FIG. 9 and FIG. 11 are examples of different types of needles (3) and stems (4) which can be coupled on the grip, with the suitable use of intermediate connectors (9A) and (9B).

The bases (8A) and (8B) are positioned longitudinally involving a cylindrical element (17) of extension similar to the grip (1) which have on their median area two cylindrical projections (18) perpendicular and opposite among themselves, and on their frontal end (23) their diameter is slightly bigger. Central cylindrical element (17) passes through hole (19) of base (8B) where two cylindrical projections (18) have a shape for corresponding to longitudinal hole (19) profile of base (8B). The activation of this mechanism, which takes place by pulling the handle (16), allows the bases (8A) and (8B) to be moved to their locking or working position.

Two helical spring-type elastic devices (20A) and (20B) are provided surrounding the cylindrical element, positioned on the back part of the respective movable bases (8A) and (8B) being the spring (20A) trimmed by a rectangular element (26) with a circular hole, cross-positioned close to the grip center (1) and the spring (20B) trimmed by the back face (27). A handle is coupled 16 on the back end of the referred cylindrical element (17).

Close to the frontal part of the mono-block are provided groups of cuts (28) on its sides, where a limiting element (29) of rectangular shape is fitted with a semi-circle shape opening and groups of cuts (30) are provided on the median area of the mono-block, where a rectangular shape limiting element (31) is fitted with a semi-circle format opening. The limiting element is an additional attribute which this type of equipment has, since it allows the surgeon to control the needle perforation depth (1.2, 2.2 mm or more). The referred limiting elements (29) and (31) are coupled on the mono-block for adjustment of the distance to certain types of needle.

On the outer and lower part of the mono-block (7) is positioned the triggering and positioning system of the needle (3) and the stem (4) which comprises a rectangular section axle (15) of upper length to the mono-block (7) and which has a trapezoid shape side cut (14A) at a distance of a third from its back end and a "V"-shaped side cut (14B) at a distance of a third from the frontal end. In these cuts, retention sliding "U"-shape elements are positioned (13A) and (13B). This system grants a higher accuracy to the surgeon when inserting and positioning the needle (3) at the desired place for collection. The difference in the geometrical form of the referred openings (14A) and (14B) provides a difference of discharge time between the stem (4) and the needle (3) in milliseconds. This time difference is vital for the procedure success since it allows the needle (3) to leave from within the stem (4) only when it's necessary for the sample collection, eliminating the risk of contamination by other tissues.

Connected to the main mono-block (7) is a mono-block longitudinal extension (33) which facilitates the locking of the system. The mono-block longitudinal extension (33) creates an interface for the coupling of the axle (15) to the mono-block (7). On the back end of the axle (15) is positioned a safety lock (21) formed by a rectangular base, with a cylinder perpendicular to its face which goes internally through the distal portion of the part of the rectangular section (15), with a perpendicular projection on the other side forming an "L", which is fitted into the traverse opening (22). When safety lock (21) is turned upward, it comes in contact with the mono-block longitudinal extension (33) to lock the system. When this is done, the system is fully stopped, allowing the surgeon to go inside the patient's body without the risk of an accidental discharge of the needle at an unsuitable place, which can cause damage to the patient. When the injury is located and the needle is necessary for collection, the surgeon has just to unlock the system and activate the frontal or back spare portion of the side longitudinal part (15), so as the system moves and the needle can, then, perform its task. Another great advantage offered by this moving system is that it enables the surgeon to operate the grip with only one of his hands. That requirement is extremely relevant, since this type of procedure is usually carried out with the aid of some other type of device which helps the surgeon to find the exact place of the sample collection, such as an ultra-sound device.

The triggering is performed in two phases; the first one carried out with the triggering of the stem, by pulling the handle up to its limit; and the second phase refers to the needle triggering, which is carried out by returning the handle to its rest position and rotating it 90 degrees to any direction and last by pulling it up to its limit again.

The handle activation is carried out by elastic forces and to trigger the device's discharge system, a force higher than the spring forces which activate the set of needles should be applied.

On the conventional handles, the stem and the needle triggering system is simultaneous, what determined a high amount of force in its triggering.

On the referred handle, the stem and needle triggering are performed independently, which renders the process easier by the simple fact that the force applied to the operation is lower.

The present invention is a useful device for not only increasing the user's safety but for providing an economical solution for retrofitting multiple biopsy needles available on the market.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

I claim:

1. A sample collector for collecting samples for biopsies to be used with at least two types of a stem and needle, each stem and needle comprising a needle extending through a stem, each type of a stem and needle having a different structure, the sample collector cooperating with the respective different structures of the at least two types of a stem and needle to operatively receive and enable the functioning of the at least two types of a stem and needle, the sample collector comprising:

a grip for serving as a housing for a selected one of at least two types of a stem and needle;
   a first movable base and a second movable base, each of the first and second movable bases being operatively mounted in said grip and comprising:
      an interchangeable connector positioning structure;
      a plurality of interchangeable connectors respectively being capable of being operatively attached to a different one of the at least two types of a stem and needle, the plurality of interchangeable connectors each comprising:
         a locating structure for cooperating with the interchangeable connector positioning structure on one of the first and second movable bases to firmly and removably position the respective interchangeable connector on the respective movable base; and
         fitting elements for cooperating with the specific structure of a specific type of a stem and needle to operatively connect the stem and needle to the respective interchangeable connector, for enabling the sample collector to operate the specific type of a stem and needle to collect the samples;
      wherein selected first and second interchangeable connectors have appropriate fitting elements for cooperating with the different structures of the selected one of the at least two types of a stem and needle for conducting a particular sample collection.

2. A sample collector according to claim 1 and further comprising:
   at least one projection extending from each of the respective movable bases;
   and the locating structure comprises:
   at least one receptacle on each of the respective interchangeable connectors for receiving the respective at least one projection;
   the respective at least one projection and the respective at least one receptacle preventing the relative movement between the respective interchangeable connector and the respective movable base.

3. A sample collector according to claim 2 wherein:
   the interchangeable connector positioning structure is the upper face for each movable base;
   the at least one projection is three cylindrical projections on each of the respective upper faces, the three cylindrical projections having progressively larger diameters; and
   the at least one receptacle is three holes in the respective interchangeable connectors for receiving the three cylindrical projections.

4. A sample collector according to claim 2 wherein the respective movable bases and the respective interchangeable connectors include a releasable holding apparatus for holding the respective interchangeable connectors on the respective movable bases when the respective interchangeable connectors are positioned on the respective movable bases.

5. A sample collector according to claim 4 wherein the releasable holding apparatus comprises at least one magnet structure on the respective movable bases, and at least one magnetic material in the respective at least one interchangeable connector.

6. A sample collector according to claim 5 wherein the at least one magnet structure comprises a plurality of holes provided on the top of each of the respective movable bases and a magnet disposed in each of the respective holes, and the at least one magnetic material comprises the at least one interchangeable connector, the at least one interchangeable connector being made from a magnetic material.

7. A sample collector according to claim 1 and further comprising a main monoblock disposed in the grip for receiving the first and second movable bases for movement in the grip, and for receiving the interchangeable connectors in operative position with the respective first and second movable bases, a selected type of stem and needle being receivable by the interchangeable connectors for operative reception on said monoblock.

8. A sample collector according to claim 1 wherein each of the first and second movable bases further comprises an upper face; and the interchangeable connector positioning structure is provided on the upper face of the respective moving bases.

9. A sample collector according to claim 1 wherein the first and second movable bases are located in the grip, and the first and second movable bases having generally cylindrical, aligned holes, each base having opposing partially cylindrical wall surfaces and an aligned, longitudinal slot between the partially cylindrical wall surfaces, and the adjacent ends of the partially cylindrical walls having transverse shoulders; and wherein the sample collector further comprises:

a longitudinal, cylindrical axle having a forward end and a rear end and extending through the bases of the first and second movable bases, the cylindrical axle comprising projections extending outwardly and dimensioned and located for sliding in the longitudinal slots of the first and second movable bases, and an enlarged forward end piece at the forward end blocking the cylindrical axle from being withdrawn from the movable base proximal the forward end, the projections extending transversely from the longitudinal, cylindrical axle for being alternatively positioned to either enable the movement of the first and second movable bases along the longitudinal, cylindrical axis or to be engageable with the transverse shoulders to lock the first and second movable bases against longitudinal movement.

10. A sample collector for collecting samples for biopsies to be used with at least two types of a stem and needle, each type of a stem and needle having a different structure, the sample collector cooperating with the respective structures of the at least two types of a stem and needle to operatively receive and enable the functioning of the at least two types of a stem and needle, the sample collector comprising:

a grip for serving as a housing for a selected one of at least two types of a stem and needle;

a first movable base and a second movable base, each movable base being operatively mounted in said grip and comprising:
an upper face;
three cylindrical projections on the upper face, the tree cylindrical projections having progressively larger diameters;
a first plurality of holes on the top of the upper face; and
a set of magnets in the first plurality of holes; and
a plurality of interchangeable connectors respectively being capable of being operatively attached to a different one of the at least two types of a stem and needle, the plurality of interchangeable connectors being magnetic and comprising:
a second plurality of holes corresponding to the respective cylindrical projections, the second plurality of holes receiving the respective cylindrical projections to removably position the interchangeable connectors on the respective first and second movable bases and being removably held on the respective movable bases by the respective set of magnets; and
fitting elements for cooperating with the specific structure of a specific type of a stem and needle to operatively connect the stem and needle to the respective interchangeable connector, for enabling the sample collector to operate the specific type of stem and needle to collect samples; and
a main monoblock disposed in the grip for receiving the first and second movable bases for movement in the grip, and for receiving the interchangeable connectors in operative position with the respective first and second movable bases, a selected type of stem and needle being receivable by the interchangeable connectors for operative reception on said monoblock.

* * * * *